United States Patent [19]

van Krieken

[11] Patent Number: 4,945,922

[45] Date of Patent: Aug. 7, 1990

[54] PACING LEAD

[75] Inventor: Frits M. van Krieken, AT Dieren, Netherlands

[73] Assignee: Vitatron Medical B.V., Dieren, Netherlands

[21] Appl. No.: 322,308

[22] Filed: Mar. 13, 1989

[51] Int. Cl.⁵ .............................................. A61N 1/05
[52] U.S. Cl. ..................................... 128/785; 128/786
[58] Field of Search ............................... 128/784–786, 128/419 P

[56] References Cited

U.S. PATENT DOCUMENTS

| | | | |
|---|---|---|---|
| 3,902,501 | 9/1975 | Citron et al. | 128/785 |
| 3,939,843 | 2/1976 | Smyth | 128/785 |
| 4,033,357 | 7/1977 | Helland et al. | 128/418 |
| 4,135,518 | 1/1979 | Dutcher | 128/419 P X |
| 4,236,529 | 12/1980 | Little | 128/785 |
| 4,301,815 | 11/1981 | Doring | 128/785 |
| 4,409,994 | 10/1983 | Doring | 128/785 |
| 4,582,069 | 4/1986 | McArthur | 128/785 |
| 4,628,944 | 12/1986 | MacGregor et al. | 128/419 P X |
| 4,669,488 | 6/1987 | Hess | 128/785 |
| 4,722,353 | 2/1988 | Sluetz | 128/785 |

*Primary Examiner*—Lee S. Cohen
*Attorney, Agent, or Firm*—Woodcock Washburn, Kurtz Mackiewicz & Norris

[57] ABSTRACT

There is provided an endocardial pacing lead having a substantially cylindrical length and an electrode at about the distal end thereof, the lead having a conductor for conducting signals between the proximal and distal ends thereof and an outer tubing enclosing the conductor for substantially the length of the lead. A tined piece is provided which envelopes the lead tubing just proximal to the distal electrode, the tined piece having a plurality of tines, each such tine being formed with a substantially C-shaped cross-section having its inner or backward surface substantially complementary to the outer surface of the tubing. The tined piece also preferably provides riser elements interspaced between respective pairs of the tines for providing a raised lead surface adjacent the tine interangles, thereby increasing the effective tined inter-radius presented to heart wall structures.

23 Claims, 3 Drawing Sheets

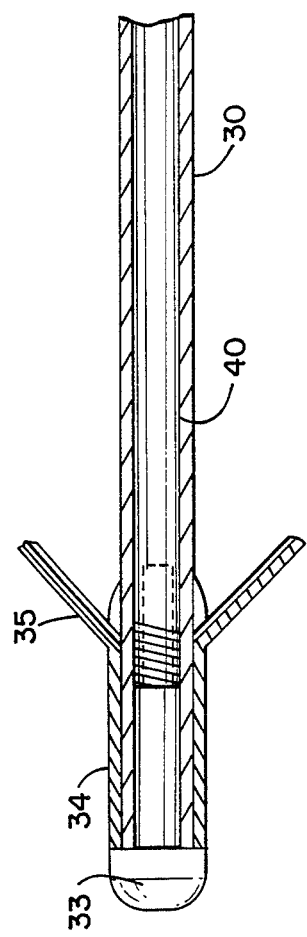
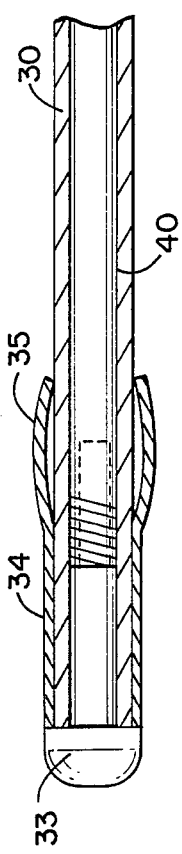
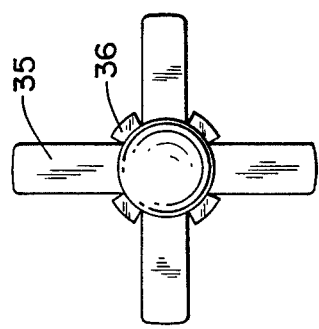
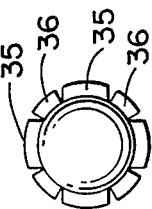

PACING LEAD

FIELD OF THE INVENTION

This invention relates to pacing leads and more particularly to pacing leads with improved features for positioning and anchoring the lead in the patient's heart.

BACKGROUND OF THE INVENTION

Endocardial pacing leads having fixation structures at or near the distal tip end are well known in the art. A widely used anchoring arrangement is that of the tined lead, where a plurality of pliant tines are disposed near the distal tip to effect good chronic anchoring after the lead tip has been optimally positioned in the heart. While the design has had some problems, the tined anchor has become the most popular passive fixation mechanism for endocardial pacemaker leads. The patent literature contains many disclosures of tined pacing leads. See, for example, U.S. Pat. Nos. 3,902,501; 3,939,843; 4,033,357; 4,236,529; 4,301,815; 4,409,994; and 5,582,069. Additionally, the non-patent pacing literature has disclosed and discussed the advantages of the tine-type anchor for chronic fixation, and the acceptance of this type of fixation mechanism in the pacing industry.

The fixation mechanism provided by tines is well understood. When heart wall growth, or trabeculae, become lodged within the acute angle formed between the tines and the tube casing, this provides a substantial anchoring effect. The tines must be designed so that they can fold down over the tubing, to reduce the introducer width at time of implanting the lead, and must be able to bend forward (distally) toward the distal tip if it is necessary to dislodge the lead during the acute stage, particularly during initial placement of the lead. This means that the tine characteristics must be chosen carefully to permit easy folding of the tine down onto the casing, and also to provide the right amount of resistance to forward bending of the tine as may be necessary during the acute stage of lead placement. It has been found that one problem that occurs during placement of the tined lead is that the tip becomes entangled in chordae connected to the heart valve, necessitating relative withdrawal of the lead and thus forward bending of the tines. Also, an obvious disadvantage of the tined structure is that when folded back upon the lead during introduction, the tines add to the thickness of the lead, i.e. increasing the introducer size.

Early tine lead designs had relatively large introducer sizes. With the venous introducer technique becoming more popular, tined lead designs were improved so that the lead would fit into smaller introducers. The introducer size of the lead is the minimum tube diameter through which a lead can be pushed with a minimum amount of friction. In practice, it has been determined primarily by: (a) the diameters of the rigid parts in the lead tip and body; (b) the elasticity of the deformable parts of the lead tip and body, since these determine friction forces; and (c) the coefficient of friction between the lead and the introducer, which can be affected by the choice of low friction materials. A classical tined anchor design is a trade-off between rigidity for good anchoring, or holding force, and flexibility for acute removability, e.g., from the chordae of papillary muscles or other unintended positions. The tine bending rigidity is substantially the same in each direction. This rigidity is an advantage when bending the tine forward, since it provides a good holding function, but it is a disadvantage when bending the tine backwards during introduction of the lead.

FIGS. 1A and 1B of this application present a representation of a prior art tined silicone lead design which is representative of the design compromises of the prior art. As can be seen in FIG. 1A, and as is conventional with tined lead construction, the normal position of the tine is to slope backward proximally from the distal tip, at an acute angle with respect to the lead casing. However, as seen in FIG. 1B, during introduction the tines must be folded backward (proximally) upon the casing, causing a substantial increase in the overall width at that point, limiting the introducer size.

Another typical problem with the prior art tined lead design is that the lead casing, either silicone tubing or PUR tubing, is not extended all the way forward to the tip. In the design of FIGS. 1A and 1B, the distal end of the coil is attached to the tip element by crimping, the crimping sleeve necessarily requiring a greater radius than that of the coil. The tined anchor piece is placed over the crimping sleeve and the silicone tubing, causing a bulge at the point of overlap with the silicone tubing. Note that this overlap is necessary in order to provide good sealing, and to prevent flow of body fluids into the coil area. Thus, the conventional crimp arrangement provides an additional limitation to reduction of the introducer size.

In practice, the tined lead as exemplified by FIG. 1A and 1B is introduced with the use of a stylet, the distal end of which presses up against the inner core piece of the tip. A problem that exists in practice is that the introduction of the stylet and the maneuvering of the lead and stylet into the heart can result in the distal end of the stylet poking through the coil near the distal tip end, which can be ruinous to the lead. It is thus advantageous to include, in any lead design, means for preventing the piercing of the distal lead end by the stylet while it is being used. The crimping sleeve solves this problem, but at the expense of introducer size.

Another design feature of importance is the inner radius R (as seen in FIG. 1A) between the tine and the longitudinal surface of the lead. In practice, this radius is a compromise. A small radius gives the best flexibility to the tine, i.e., reduces its stiffness to bending in either direction. If the design anticipates the placement of the lead will involve undesired catching of heart wall structures, e.g. chordae, a larger radius is desired to better permit the heart structure to bend the tine forward, for extraction of the lead. However, a larger inner radius R will negatively affect the bending capability of the tine, and will increase the introducer size The tined lead of FIGS. 1A and 1B, made commercially by the assignee of this application, fits into a 13 F introducer with its tines folded backward Further tine flattening permits reduction to an 11 F size. Since the body size is 5.5 F, the introducer size is seen to be twice as great. By contrast, the objective of the lead of this design is an 8F introducer size for a silicone lead, and a 6F size for a lead made with PUR 55D.

There thus have existed a number of problems associated with lead tip design, which the design of the instant invention reduces. The problem of introducer thickness is achieved by an improvement in the cross-sectional design of the tine and by extending the lead tubing all the way to the forward portion of the tip element. Instead of crimping the end electrode piece to the coil, the inside of the electrode is spot welded to the distal end of the coil, enabling extending the lead tubing all the way to the tip end. The problem of optimally selecting the inner radius R is alleviated by the introduction of riser elements between respective pairs of tines. Further, the problem of ensuring against piercing the lead during use of the stylet is reduced by providing a sheathing around the coil for a distance proximal to where the coil is attached to the tip element.

SUMMARY OF THE INVENTION

The objects of this invention are to overcome the above-recited prior art problems, and to provide design solutions with advantages not heretofore available.

The invention comprises an endocardial pacing lead having a substantially cylindrical length and an electrode at about the distal end thereof, the lead length having a conductor for conducting signals between the proximal and distal ends thereof and an outer tubing enclosing the conductor for substantially the length of the lead, and a tined piece enveloping the lead end tubing just proximal to the distal electrode, the tined piece having a plurality of tines, each such tine being formed with a C-shaped cross-section having a concave inner surface substantially complementary to the outer surface of the tubing. The tined piece also preferably provides riser elements interspaced between respective pairs of the tines, for providing a raised surface adjacent the tine inner angles, thereby increasing the effective tine inner radius presented to heart wall structures. Also, the design provides for a sheath surrounding the coil and extending a limited length proximal from the area where the coil is attached to the electrode tip, the sheath providing resistance to penetration through the coil area by a stylet.

BRIEF DESCRIPTION OF THE DRAWINGS

FIG. 2B is a cross-sectional representative view of the distal portion of the lead of this invention, with the tines in a normal working position;

FIG. 2C is a front end view of the tip of the lead of this invention, illustrating the relationship of the tines and the riser elements;

FIG. 2D is a cross sectional view of a tine of this invention;

FIG. 2E is a cross-sectional representative view of the distal portion of the same lead as FIG. 2B, but with the tines folded backward into the introducer position;

FIG. 2F is a front view of the lead of FIG. 2E; and

DESCRIPTION OF THE PREFERRED EMBODIMENTS

Figure 1A:
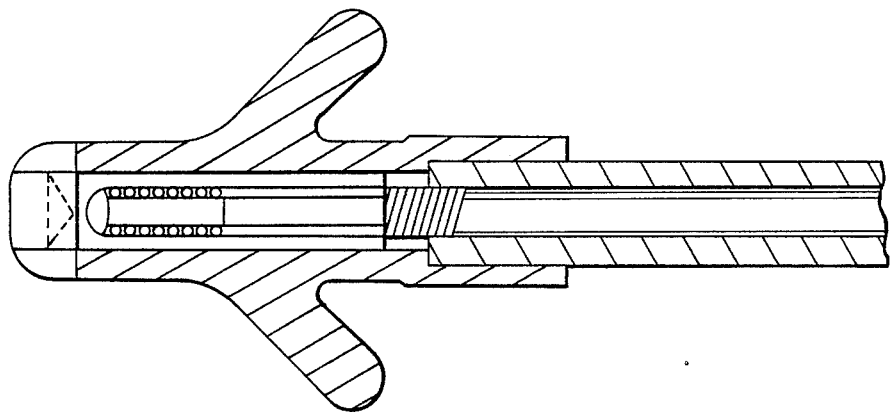
FIG. 1A is a cross-sectional representation of a prior art tined lead design, with the tines in a normal position forming an acute angle with the lead length.
Figure 1B:
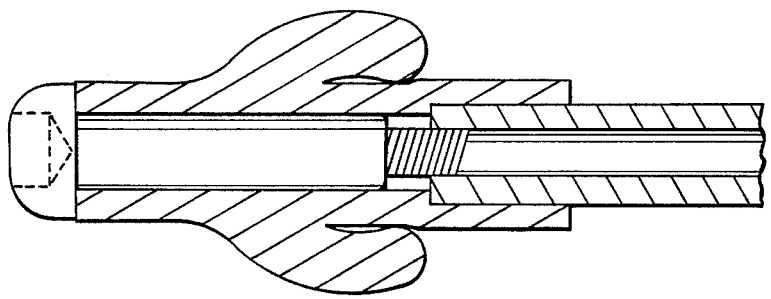
FIG. 1B is a cross-sectional schematic representation of the same lead as illustrated in FIG. 1A, showing the tine folded backward for introduction.
Figure 2A:
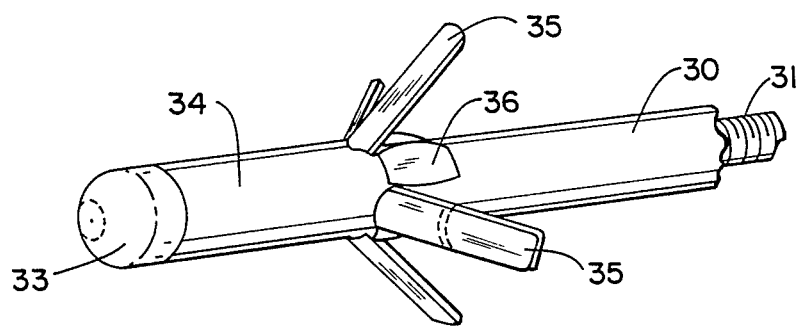
FIG. 2A is a perspective view of the distal portion of the lead of this invention, illustrating the tines and the interspaced risers.

Referring now to FIG. 2A, there is shown a perspective view of the distal end portion of the lead of this invention. The tip electrode surface is shown at 33. It is noted that the electrode surface as such is not a feature of the invention, the design permitting any electrode surface which is consistent with the reduced diameter of the lead. Of course, a second electrode, for bipolar systems, may be used within the scope of the invention.

A tined piece 34 is shown, made of silicone rubber or preferably from a rigid material having good frictional properties. Examples of acceptable materials include polyurethanes such as those sold under trademark designations PUR 55D, PUR 75D, PE and PTFE, where the numbers indicate Shore D harness. The piece 34 has a cylindrical tube portion which has at its proximal end a plurality of tines 35 spaced circumferentially from each other, and interspaced risers 36. In accordance with this invention each tine has a C-shaped cross-section, as seen in FIG. 2D, which provides good stiffness against bending forward, i.e. in the distal direction, but which buckles easily in the backwards or proximal direction. The C-shaped cross-section provides the requisite forward stiffness with a thinner tine wall, such that the thickness of the tines can be reduced over the prior art. The C-shaped cross-section is complementary to and closely follows the outer cylindrical periphery of the casing 30, such that it adds very little to the introducer size of the lead. The thickness of the tube portion of the tined piece 34, distal to the tines, is likewise reduced in this design. For example, the actual tine thickness may be only 0.15 mm, as indicated in FIG. 2D.

Referring to FIGS. 2B and 2C, there are shown additional views of the distal end portion of the lead of this invention. For a lead design using PUR 55D tubing, the coil diameter is suitably 0.8 mm, and the outer diameter of the tubing, or casing 30, is 1.22 mm. Note that the casing 30 extends through to the tip end of the exposed surface portion of electrode 33, to provide continual sealing of the lead, regardless of whether the tines have degraded. The thin-walled tined piece 34 is glued around the end of the tubing, providing a smooth contiguous surface from the exposed electrode tip backwards. The tines are suitably displaced at about a 45° angle. The risers 36 are illustrated in FIG. 2C as being spaced between adjacent pairs of tines 34. The risers provide the function of elevating thinner heart wall elements such as chordae from the lead surface without effectively increasing the introducer size, as is described more fully below in connection with FIGS. 3A, 3B and 3C.

Referring now to FIGS. 2E and 2F, the lead of this invention is illustrated in its introducer position, i.e. with the tines flattened down against the casing 30. For the tine as shown, the overall introducer size in the folded back position is about 2.0 mm, a considerable advantage over existing lead designs.

It is noted that the design does not include a crimping bush. Instead, the coils are laser spot welded to the electrode core 38. The absence of the conventional crimping bush introduces the risk of stylet perforation just behind, or proximal to the electrode core element. In one embodiment of this invention, the adjoining coil windings at the free distal end of the coil are laser spot-welded to one another, to provide a sealed cylinder through which the stylet cannot penetrate. In another embodiment, a very thin-walled casing of PTFE shrink tubing, illustrated at 40, is placed around the free end of the coil, both stiffening and encapsulating the coil. When the shrink tubing is shrunk onto the coil, it penetrates into the areas between the coil loops, providing the desired continuous encasing. The lead of this invention may, of course, be made with other materials. A silicone lead in accordance with the design of this invention has an outer casing diameter of 1.73 mm, and a distal tip diameter at the electrode and the tined piece of 2.2 mm. The overall introducer size, with the tines folded back, is about 2.6 mm. The invention permits a lead of about 8F using silicone tubing and about 6F using 55 Shore D polyurethane (PUR 55D) tubing.

Figure 3A:
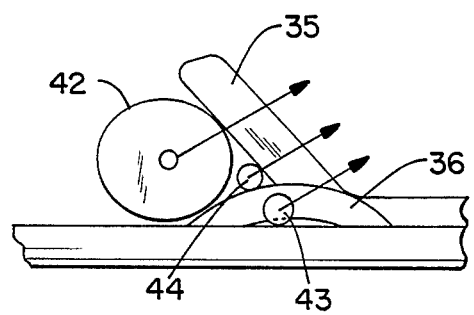
FIG. 3A is a diagrammatic sketch showing the relation of the riser elements to the tines.
Figure 3B:
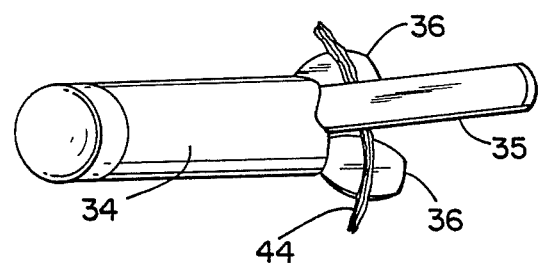
FIG. 3B is a perspective sketch showing the elevating function of the riser elements.
Figure 3C:
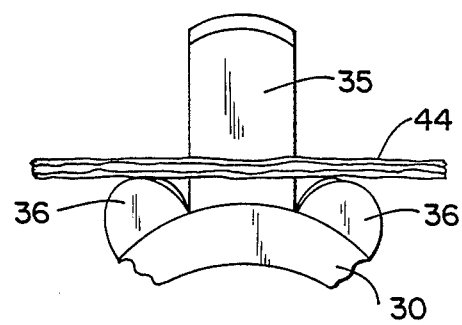
FIG. 3C is a diagrammatic sketch showing the action of the riser elements as seen from a position proximal to the tines.

Referring now to FIGS. 3A, 3B and 3C, there is illustrated the manner by which the risers aid in the object of preventing small structures such as chordae from getting caught too close to the base of the tines. The holding force of the tine against backward withdrawal of the lead is greatest with respect to small diameter structures, and lessens as the diameter increases. FIG. 3A shows the moment arms, indicated as arrows, for different heart wall structures. A relatively larger heart wall structure, such as the trabecula illustrated at 42, does not seat so far down into the intersection of the tine and the casing, and presents a reasonable good lever arm to bend the tine backward. On the other hand, smaller structures, such as chordae, one of which is illustrated at 43, can be positioned down close to the base of the tine, and present virtually no lever arm for pulling the tine backward. Thus, in practice with conventional tined leads, the lead can be withdrawn for replacement relatively easily if the trabeculae are caught in the tine intersection, but with much greater difficulty if the lead is caught by chordae.

FIGS. 3B and 3C further illustrate the positioning of the chordae with respect to the tube casing for the lead of this invention, showing that the chordae lie somewhat tangentially over a pair of risers, which risers are elevated away from the tube casing so that the chordae 44 has a greater mechanical advantage. The risers are flexible elements, preferably made integrally with the tines, and formed to normally project radially from the cylindrical surface of the lead. The risers are formed so that their point of peak elevation is proximal, i.e., back from the tine base and lateral to each tine angle. By so placing the risers, the chordae are held at an elevated position relative to the tine base, which is the equivalent of giving the tines an effective greater inner radius. Of course, the tines can be made with a conveniently smaller inner radius, so that the detrimental effect of a small inner radius is reduced without comprising the flexibility of the tines. As seen in the view of FIG. 3C, looking toward the distal tip from a point proximal to the tines, the risers provide bulges that project radially outward and lift chordae away from the casing 30. The risers must have sufficient height to keep the chordae elevated with respect to the backside of the tine, but clearly cannot rise as high as the tines. Further, they cannot be too large or they will increase the introducer size. By making the risers about the same thickness as the tines, they don't add to the introducer size, as seen in FIG. 2F.

I claim:

1. A pacing lead having proximal and distal ends, a substantially cylindrical length between said ends, and an electrode at about the distal end thereof, said length having a conductor connected to said electrode for conducting signals between said proximal end and said electrode and an outer tubing enclosing said conductor, characterized by an integral tined piece enveloping said tubing just proximal to said electrode, said piece having a plurality of tines extending radially and proximally from said tubing, each such tine being formed with a C-shaped cross-section having a concave inner surface substantially complementary to the adjacent surface of said tubing.

2. The pacing lead of claim 1, wherein said tubing extends to said electrode, and said piece comprises a casing portion extending a predetermined distance proximal from said electrode and said tines extend from said casing portion, said tines normally extending at an acute angle from the axis of said tubing.

3. The pacing lead of claim 2, wherein said tined piece has a wall thickness of less than about 0.25 mm.

4. The pacing lead of claim 3, wherein said tined piece is made from a relatively rigid polyurethane material.

5. The pacing lead of claim 2, wherein said tined piece comprises shallow riser members extending longitudinally from said casing portion and positioned between respective pairs of tines.

6. The pacing lead of claim 5, wherein said riser members extend radially outward a distance no greater than that of said tines when they are folded against the tubing surface, whereby they do not increase the introducer size of said lead.

7. The pacing lead of claim 2, wherein said conductor is a coil, and said electrode is spot welded to the inside of a distal end of said coil.

8. The pacing lead of claim 1, wherein said tubing is made of a silicone rubber.

9. The pacing lead of claim 1, wherein said tubing is made of a polyurethane.

10. The pacing lead of claim 1, wherein said tubing has a predetermined outer curvature and said tines have a radius of curvature that is approximately the same as said predetermined curvature, so that when said tines are compressed against said tubing the increase of the tines to the introducer size of the lead is very small.

11. A pacing lead for conducting signals between a pacemaker and a patient's heart, said lead having a proximal end and a distal end, a substantially cylindrical casing extending substantially from said proximal end to said distal end, an electrode at about said distal end and a conductor connected to said electrode for conducting signals between said proximal end and said electrode, and further having an anchoring means near its distal end for anchoring the lead with respect to a heart wall, said anchoring means comprising a plurality of tines which normally extend proximally and radially away from said lead so that they form an acute angle thereto, said tines being joined to said lead at respective tine positions spaced substantially circumferentially from one another, and further having respective riser means located between pairs of said tines for raising heart structures radially relative to said tines.

12. The pacing lead of claim 11, wherein each of said riser means comprises a flexible member which normally presents an effective raised lead surface just back from the tine positions between which it is located.

13. The pacing lead of claim 12, wherein each of said riser means is sufficiently flexible that it can be pressed down onto said casing so as not to add to the introducer width of said lead.

14. The pacing lead of claim 11, wherein said electrode presents an exposed conductive surface, said casing extending to said electrode surface, and said anchoring means comprising a cylindrical portion which envelopes said casing and which abuts said electrode surface.

15. The pacing lead of claim 14, wherein said conductor comprises a coil, said electrode having an unexposed core portion which extends proximally within a distal end of said conductor, said conductor being spot welded to said core portion.

16. The pacing lead of claim 15, comprising a thin-walled tubing surrounding said conductor in the area where it is welded to said electrode core portion, for a short length proximal thereto.

17. The pacing lead of claim 11, wherein said tines have a C-shaped cross-section having a relatively concave inner surface with the relatively concave surfaces being toward the lead casing.

18. The pacing lead of claim 11, wherein both said casing and said anchoring means are made of the same material, said anchoring means being fixed around the distal end of said casing with adhesive.

19. The pacing lead of claim 18, wherein said material is a polyurethane.

20. A pacing lead having proximal and distal ends and a substantially cylindrical length therebetween, a coil extending substantially said length for carrying signals between said proximal and distal ends, an electrode positioned at about said distal end and connected to said coil, and a lead casing of a predetermined radius covering said coil, said lead being further characterized by an anchoring means at about said distal end which comprises a plurality of circumferentially spaced tines and riser elements positioned laterally between said tines, said riser elements presenting a surface having an effective radius greater than said casing radius but less than the normal radial extension of said tines.

21. The pacing lead of claim 20, wherein each said tine extends proximally and radially away from the lead, making an acute angle with the lead at an intersecting position defining an inner tine angle, and each said riser element comprises a normally bulging element which has a peak radial extension at a position just proximal to the tines between which it is spaced, thereby effectively increasing the inner tine angle presented to smaller thickness heart wall elements.

22. The pacing lead of claim 20, wherein said electrode has an exposed surface and said lead casing extends substantially to said exposed surface of said electrode, and said anchoring means has a casing portion which envelopes the distal end of said lead casing.

23. An endocardial pacing lead having proximal and distal ends, a substantially cylindrical length therebetween, and an electrode at about said distal end, the lead length having a conductor connected to said electrode for conducting signals between said proximal end and said electrode and an outer tubing enclosing the conductor for substantially the length of the lead, and a plurality of tines positioned circumferentially just proximal to the distal electrode, each such tine extending proximally and radially from said tubing and being formed with a substantially C-shaped cross-section having a concave inner surface substantially complementary to the outer surface of the tubing.

* * * * *